United States Patent [19]

Vaccaro et al.

[11] Patent Number: 5,656,624
[45] Date of Patent: Aug. 12, 1997

[54] 4-[(HETEROCYCLOALKYL OR HETEROAROMATIC)-SUBSTITUTED PHENYL]-2-AZETIDINONES USEFUL AS HYPOLIPIDEMIC AGENTS

[75] Inventors: Wayne D. Vaccaro, Yardley, Pa.; Duane A. Burnett, Fanwood; John W. Clader, Cranford, both of N.J.

[73] Assignee: Schering Corporation, Kenilworth, N.J.

[21] Appl. No.: 361,265

[22] Filed: Dec. 21, 1994

[51] Int. Cl.[6] .................. A61K 31/395; C07D 205/08; C07D 205/12; C07D 413/10
[52] U.S. Cl. .................. 514/210; 540/200; 540/203
[58] Field of Search .................. 540/200; 514/210

[56] References Cited

U.S. PATENT DOCUMENTS

| | | | |
|---|---|---|---|
| 4,680,391 | 7/1987 | Firestone et al. | 540/200 |
| 4,983,597 | 1/1991 | Yang et al. | 514/210 |
| 5,120,729 | 6/1992 | Chabala et al. | 514/210 |

FOREIGN PATENT DOCUMENTS

| | | |
|---|---|---|
| 199630 | 10/1986 | European Pat. Off. . |
| 264231 | 4/1988 | European Pat. Off. . |
| 337549 | 10/1989 | European Pat. Off. . |
| 93/02048 | 2/1993 | WIPO . |
| 94/14433 | 7/1994 | WIPO . |
| WO94/17038 | 8/1994 | WIPO . |
| WO95/08532 | 3/1995 | WIPO . |

OTHER PUBLICATIONS

*Atherosclerosis*, 115 (1995), pp. 45–63.
*Biochemical Pharmacology*, 47, 9 (1994), pp. 1545–1551.
Bentley, et al, *J. Chem Soc., Perkin Trans. I*, 16 (1976), pp. 1725–1734.
Shufan et al, *Chemical Abstracts*, 114, 15 (1991), Abstract No. 142930z.
Ram et al, *Indian J. Chem., Sect B*, 29B 12 (1990), pp. 1134–1137.
Witzum, *Circulation*, 80, 5 (1989), pp. 1101–1114.
Illingworth, *Drugs*, 36(Supp. 3) (1988), pp. 63–71.
Allain, et al, *Clin. Chem.*, 20, (1974), pp. 470–475.

Schnitzer–Polokoff, et al, *Comp. Biochem. Physiol.*, 99A (1991), pp. 665–670.
Horie, et al, *Atherosclerosis*, 88 (1991), pp. 183–192.
Baxter, et al, *J. Biological Chem.*, 267, 17 (1992), pp. 11705–11708.
*Current Drugs: Anti–Atherosclerotic Agnets* —Summary Factfile, May, 1992.
Harwood, et al., *Journal of Lipid Research*, 34 (1993), pp. 377–395.

Primary Examiner—Mark L. Berch
Attorney, Agent, or Firm—Anita W. Magatti

[57] ABSTRACT

4-[(Heterocycloalkyl or heteroaromatic)-substituted phenyl] -2-azetidinone hypocholesterolemic agents of the formula

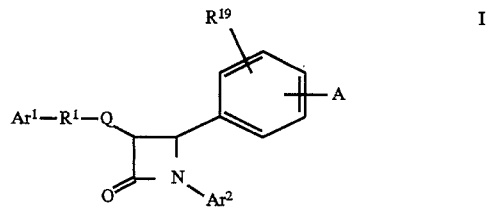

or a pharmaceutically acceptable salt thereof, wherein:

A is optionally substituted heterocycloalkyl, heteroaryl, benzofused heterocycloalkyl, or benzofused heteroaryl;

$Ar^1$ and $Ar^2$ are optionally substituted aryl;

Q is a bond or, with the 3-position ring carbon of the azetidinone, forms a spiro group; and $R^1$ is alkylene; alkylene wherein a carbon in the chain is replaced by —O—, —C(O)—, phenylene, —$NR^8$—, —$S(O)_{0-2}$— or cycloalkylene; or alkenylene; or, when Q is a bond, $R^1$ can be alkylene substituted by one or two hydroxy groups or hydroxy derivatives, wherein the alkylene chain can optionally be joined to $Ar^1$ through —O— or —$S(O)_{0-2}$— or joined to the azetidinone ring through a —$S(O)_{0-2}$— group;

a method of lowering serum cholesterol by administering said compounds, pharmaceutical compositions containing them, and the combination of a substituted azetidinone and a cholesterol biosynthesis inhibitor for the treatment and prevention of atherosclerosis.

3 Claims, No Drawings

4-[(HETEROCYCLOALKYL OR HETEROAROMATIC)-SUBSTITUTED PHENYL]-2-AZETIDINONES USEFUL AS HYPOLIPIDEMIC AGENTS

BACKGROUND OF THE INVENTION

The present invention relates to 4-[(heterocycloalkyl or heteroaromatic)-substituted phenyl]-2-azetidinones useful as hypocholesterolemic agents in the treatment and prevention of atherosclerosis, and to the combination of a 4-[(heterocycloalkyl or heteroaromatic)-substituted phenyl]-2-azetidinone of this invention and a cholesterol biosynthesis inhibitor for the treatment and prevention of atherosclerosis.

Atherosclerotic coronary heart disease represents the major cause for death and cardiovascular morbidity in the western world. Risk factors for atherosclerotic coronary heart disease include hypertension, diabetes mellitus, family history, male gender, cigarette smoke and serum cholesterol. A total cholesterol level in excess of 225–250 mg/dl is associated with significant elevation of risk.

Cholesteryl esters are a major component of atherosclerotic lesions and the major storage form of cholesterol in arterial wall cells. Formation of cholesteryl esters is also a key step in the intestinal absorption of dietary cholesterol.

A few azetidinone compounds have been reported as being useful in lowering cholesterol and/or in inhibiting the formation of cholesterol-containing lesions in mammalian arterial walls. U.S. Pat. No. 4,983,597 discloses N-sulfonyl-2-azetidinones as anticholesterolemic agents and Ram, et al., in *Indian J Chem.*, Sect. B, 29B, 12 (1990), p. 1134–7, disclose ethyl 4-(2-oxoazetidin-4-yl)phenoxy-alkanoates as hypolipidemic agents. European Patent Publication 264,231 discloses 1-substituted-4-phenyl-3-(2-oxoalkylidene)-2-azetidinones as blood platelet aggregation inhibitors. European Patent 199,630 and European Patent Application 337,549 disclose elastase inhibitory substituted azetidinones said to be useful in treating inflammatory conditions resulting in tissue destruction which are associated with various disease states, e.g. atherosclerosis. WO93/02048 discloses substituted β-lactams useful as hypocholesterolemic agents.

In addition to regulation of dietary cholesterol, the regulation of whole-body cholesterol homeostasis in humans and animals involves modulation of cholesterol biosynthesis, bile acid biosynthesis, and the catabolism of the cholesterol-containing plasma lipoproteins. The liver is the major organ responsible for cholesterol biosynthesis and catabolism and, for this reason, it is a prime determinant of plasma cholesterol levels. The liver is the site of synthesis and secretion of very low density lipoproteins (VLDL) which are subsequently metabolized to low density lipoproteins (LDL) in the circulation. LDL are the predominant cholesterol-carrying lipoproteins in the plasma and an increase in their concentration is correlated with increased atherosclerosis.

When cholesterol absorption in the intestines is reduced, by whatever means, less cholesterol is delivered to the liver. The consequence of this action is a decreased hepatic lipoprotein (VLDL) production and an increase in the hepatic clearance of plasma cholesterol, mostly as LDL. Thus, the net effect of an inhibition of intestinal cholesterol absorption is a decrease in plasma cholesterol levels.

The inhibition of cholesterol biosynthesis by 3-hydroxy-3-methylglutaryl coenzyme A reductase (EC1.1.1.34) inhibitors has been shown to be an effective way to reduce plasma cholesterol (Witzum, *Circulation*, 80, 5 (1989), p. 1101–1114) and reduce atherosclerosis. Combination therapy of an HMG CoA reductase inhibitor and a bile acid sequestrant has been demonstrated to be more effective in human hyperlipidemic patients than either agent in monotherapy (Illingworth, *Drugs*, 36 (Suppl. 3) (1988), p. 63–71).

SUMMARY OF THE INVENTION

Compounds of the present invention are represented by the formula I

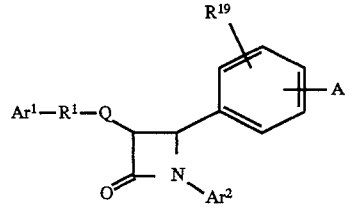

or a pharmaceutically acceptable salt thereof, wherein

A is selected from the group consisting of $R^2$-substituted heterocycloalkyl, $R^2$-substituted heteroaryl, $R^2$-substituted benzofused heterocycloalkyl, and $R^2$-substituted benzofused heteroaryl;

$Ar^1$ is aryl or $R^3$-substituted aryl;

$Ar^2$ is aryl or $R^4$-substituted aryl;

Q is a bond or with the 3-position ring carbon of the azetidinone, forms the spiro group

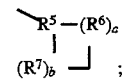

and $R^1$ is selected from the group consisting of

—$(CH_2)_q$—, wherein q is 2–6, provided that when Q forms a spiro ring, q can also be zero or 1;

—$(CH_2)_e$-G-$(CH_2)_r$—, wherein G is —O—, —C(O)—, phenylene, —$NR^8$— or —$S(O)_{0-2}$—, e is 0–5 and r is 0–5, provided that the sum of e and r is 1–6;

—($C_2$-$C_6$ alkenylene)—; and

—$(CH_2)_f$-V-$(CH_2)_g$—, wherein V is $C_3$-$C_6$ cycloalkylene, f is 1–5 and g is 0–5, provided that the sum of f and g is 1–6;

$R^5$ is

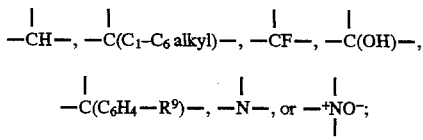

$R^6$ and $R^7$ are independently selected from the group consisting of —$CH_2$—, —CH($C_1$-$C_6$ alkyl)-, —C(di-($C_1$-$C_6$) alkyl), —CH=CH— and —C($C_1$-$C_6$ alkyl)=CH—; or $R^5$ together with an adjacent $R^6$, or $R^5$ together with an adjacent $R^7$, form a —CH=CH— or a —CH=C($C_1$-$C_6$ alkyl)- group;

a and b are independently 0, 1, 2 or 3, provided both are not zero; provided that when $R^6$ is —CH=CH— or —C($C_1$-$C_6$ alkyl)=CH—, a is 1; provided that when $R^7$ is —CH=CH— or —C($C_1$-$C_6$ alkyl)=CH—, b is 1; provided that when a is 2 or 3, the $R^6$'s can be the same or different; and provided that when b is 2 or 3, the $R^7$'s can be the same or different;

and when Q is a bond, $R^1$ also can be:

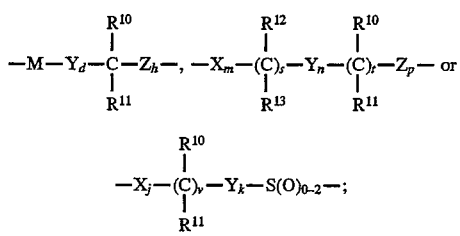

M is —O—, —S—, —S(O)— or —S(O)$_2$—;

X, Y and Z are independently selected from the group consisting of —CH$_2$—, —CH(C$_1$-C$_6$ alkyl)- and —C(di-(C$_1$-C$_6$) alkyl);

$R^{10}$ and $R^{12}$ are independently selected from the group consisting of —OR$^{14}$, —O(CO)R$^{14}$, —O(CO)OR$^{16}$ and —O(CO)NR$^{14}$R$^{15}$; $R^{11}$ and $R^{13}$ are independently selected from the group consisting of hydrogen, (C$_1$-C$_6$)alkyl and aryl; or $R^{10}$ and $R^{11}$ together are =O, or $R^{12}$ and $R^{13}$ together are =O;

d is 1, 2 or 3;

h is 0, 1, 2, 3 or 4;

s is 0 or 1; t is 0 or 1; m, n and p are independently 0–4; provided that at least one of s and t is 1, and the sum of m, n, p, s and t is 1–6; provided that when p is 0 and t is 1, the sum of m, s and n is 1–5; and provided that when p is 0 and s is 1, the sum of m, t and n is 1–5;

v is 0 or 1;

j and k are independently 1–5, provided that the sum of j, k and v is 1–5;

$R^2$ is 1–3 substituents on the ring carbon atoms selected from the group consisting of hydrogen, (C$_1$-C$_{10}$)alkyl, (C$_2$-C$_{10}$)alkenyl, (C$_2$-C$_{10}$)alkynyl, (C$_3$-C$_6$)cycloalkyl, (C$_3$-C$_6$)cycloalkenyl, R$^{17}$-substituted aryl, R$^{17}$-substituted benzyl, R$^{17}$-substituted benzyloxy, R$^{17}$-substituted aryloxy, halogeno, —NR$^{14}$R$^{15}$, NR$^{14}$R$^{15}$ (C$_1$-C$_6$ alkylene)-, NR$^{14}$R$^{15}$C(O)(C$_1$-C$_6$ alkylene)-, —NHC(O)R$^{16}$, OH, C$_1$-C$_6$ alkoxy, —OC(O)R$^{16}$, —COR$^{14}$, hydroxy(C$_1$-C$_6$)alkyl, (C$_1$-C$_6$)alkoxy (C$_1$-C$_6$)alkyl, NO$_2$, —S(O)$_{0-2}$R$^{16}$, —SO$_2$NR$^{14}$R$^{15}$ and —(C$_1$-C$_6$ alkylene)COOR$^{14}$; when $R^2$ is a substituent on a heterocycloalkyl ring, $R^2$ is as defined, or is =O or

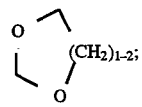

and, where $R^2$ is a substituent on a substitutable ring nitrogen, it is hydrogen, (C$_1$-C$_6$)alkyl, aryl, (C$_1$-C$_6$) alkoxy, aryloxy, (C$_1$-C$_6$)alkylcarbonyl, arylcarbonyl, hydroxy, —(CH$_2$)$_{1-6}$CONR$^{18}$R$^{18}$,

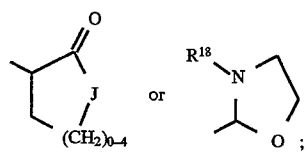

J is —O—, —NH—, —NR$^{18}$— or —CH$_2$—;

$R^3$ and $R^4$ are independently selected from the group consisting of 1–3 substituents independently selected from the group consisting of (C$_1$-C$_6$)alkyl, —OR$^{14}$, —O(CO)R$^{14}$, —O(CO)OR$^{16}$, —O(CH$_2$)$_{1-5}$OR$^{14}$, —O(CO)NR$^{14}$R$^{15}$, —NR$^{14}$R$^{15}$, —NR$^{14}$(CO)R$^{15}$, —NR$^{14}$(CO)OR$^{16}$, —NR$^{14}$(CO)NR$^{15}$R$^{19}$, —NR$^{14}$SO$_2$R$^{16}$, —COOR$^{14}$, CONR$^{14}$R$^{15}$, —COR$^{14}$, —SO$_2$NR$^{14}$R$^{15}$, S(O)$_{0-2}$R$^{16}$, —O(CH$_2$)$_{1-10}$—COOR$^{14}$, —O(CH$_2$)$_{1-10}$CONR$^{14}$R$^{15}$, —(C$_1$-C$_6$ alkylene)-COOR$^{14}$, —CH=CH—COOR$^{14}$, —CF$_3$, —CN, —NO$_2$ and halogen;

$R^8$ is hydrogen, (C$_1$-C$_6$)alkyl, aryl (C$_1$-C$_6$)alkyl, —C(O)R$^{14}$ or —COOR$^{14}$;

$R^9$ and $R^{17}$ are independently 1-3 groups independently selected from the group consisting of hydrogen, (C$_1$-C$_6$)alkyl, (C$_1$-C$_6$)alkoxy, —COOH, NO$_2$, —NR$^{14}$R$^{15}$, OH and halogeno;

$R^{14}$ and $R^{15}$ are independently selected from the group consisting of hydrogen, (C$_1$-C$_6$)alkyl, aryl and aryl-substituted (C$_1$-C$_6$)alkyl;

$R^{16}$ is (C$_1$-C$_6$)alkyl, aryl or R$^{17}$-substituted aryl;

$R^{18}$ is hydrogen or (C$_1$-C$_6$)alkyl; and $R^{19}$ is hydrogen, hydroxy or (C$_1$-C$_6$)alkoxy.

"A" is preferably an R$^2$-substituted, 6-membered heterocycloalkyl ring containing 1 or 2 nitrogen atoms. Preferred heterocycloalkyl rings are piperidinyl, piperazinyl and morpholinyl groups. The ring "A" is preferably joined to the phenyl ring through a ring nitrogen. Preferred R$^2$ substituents are hydrogen and lower alkyl. $R^{19}$ is preferably hydrogen.

Ar$^2$ is preferably phenyl or R$^4$-phenyl, especially (4-R$^4$)-substituted phenyl. Preferred definitions of $R^4$ are lower alkoxy, especially methoxy, and halogeno, especially fluoro.

Ar$^1$ is preferably phenyl or R$^3$-substituted phenyl, especially (4-R$^3$)-substituted phenyl.

There are several preferred definitions for the -R$^1$-Q- combination of variables:

Q is a bond and $R^1$ is lower alkylene, preferably propylene;

Q is a spiro group as defined above, wherein preferably $R^6$ and $R^7$ are each ethylene and $R^5$ is

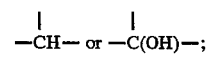

Q is a bond and $R^1$ is

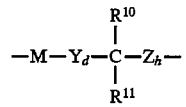

wherein the variables are chosen such that $R^1$ is —O—CH$_2$—CH(OH)—;

Q is a bond and $R^1$ is

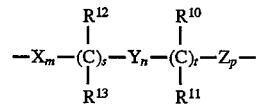

wherein the variables are chosen such that $R^1$ is —CH(OH)—(CH$_2$)$_2$—; and

Q is a bond and R¹ is

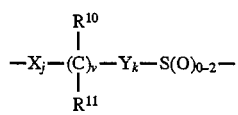

wherein the variables are chosen such that R¹ is —CH(OH)—CH₂—S(O)₀₋₂—.

This invention also relates to the use of a compound of formula I as a hypocholesterolemic agent in a mammal in need of such treatment.

In another aspect, the invention relates to a pharmaceutical composition comprising a substituted azetidinone of formula I in a pharmaceutically acceptable carrier.

The present invention also relates to a method of reducing plasma cholesterol levels, and to a method of treating or preventing atherosclerosis, comprising administering to a mammal in need of such treatment an effective amount of a combination of a 4[(heterocycloalkyl or heteroaromatic)-substituted phenyl]-2-azetidinone cholesterol absorption inhibitor of this invention and a cholesterol biosynthesis inhibitor. That is, the present invention relates to the use of a 4[(heterocycloalkyl or heteroaromatic)-substituted phenyl]-2-azetidinone cholesterol absorption inhibitor for combined use with a cholesterol biosynthesis inhibitor (and, similarly, use of a cholesterol biosynthesis inhibitor for combined use with a 4[(heterocycloalkyl or heteroaromatic)-substituted phenyl]-2-azetidinone cholesterol absorption inhibitor) to treat or prevent athersclerosis or to reduce plasma cholesterol levels.

In yet another aspect, the invention relates to a pharmaceutical composition comprising an effective amount of a 4[(heterocycloalkyl or heteroaromatic)-substituted phenyl]-2-azetidinone cholesterol absorption inhibitor, a cholesterol biosynthesis inhibitor, and a pharmaceutically acceptable carrier. In a final aspect, the invention relates to a kit comprising in one container an effective amount of a 4[(heterocycloalkyl or heteroaromatic)-substituted phenyl]-2-azetidinone cholesterol absorption inhibitor in a pharmaceutically acceptable carrier; and in a separate container, an effective amount of a cholesterol biosynthesis inhibitor in a pharmaceutically acceptable carrier.

DETAILED DESCRIPTION

As used herein, the term "alkyl" or "lower alkyl" means straight or branched alkyl chains of 1 to 6 carbon atoms and "alkoxy" similarly refers to alkoxy groups having 1 to 6 carbon atoms.

"Alkenyl" means straight or branched carbon chains having one or more double bonds in the chain, conjugated or unconjugated. Similarly, "alkynyl" means straight or branched carbon chains having one or more triple bonds in the chain. Where an alkyl, alkenyl or alkynyl chain joins two other variables and is therefore bivalent, the terms alkylene, alkenylene and alkynylene are used.

"Cycloalkyl" means a saturated carbon ring of 3 to 6 carbon atoms, while "cycloalkylene" refers to a corresponding bivalent ring, wherein the points of attachment to other groups include all positional isomers.

"Halogeno" refers to fluorine, chlorine, bromine or iodine radicals.

"Aryl" means phenyl, naphthyl, indenyl, tetrahydronaphthyl or indanyl. "Phenylene" means a bivalent phenyl group, including ortho, meta and para-substitution. R¹⁷-benzyl and R¹⁷-benzyloxy refer to benzyl and benzyloxy radicals which are substituted on the phenyl ring.

"Heterocycloalkyl" means a 3- to 7-membered saturated ring containing a nitrogen atom, optionally containing one aditional heteroatom selected from the group consisting of N, O and S(O)₀₋₂, and optionally containing a double bond between a ring nitrogen and an adjacent carbon. The heterocycloalkyl ring is substituted on one or more ring carbon or nitrogen atoms by a variable R² as defined above. "Benzofused heterocycloalkyl" refers to heterocycloalkyl groups as defined wherein a benzene radical is joined to adjacent carbon atoms. Typical heterocycloalkyl and benzofused heterocycloalkyl groups are exemplified as shown:

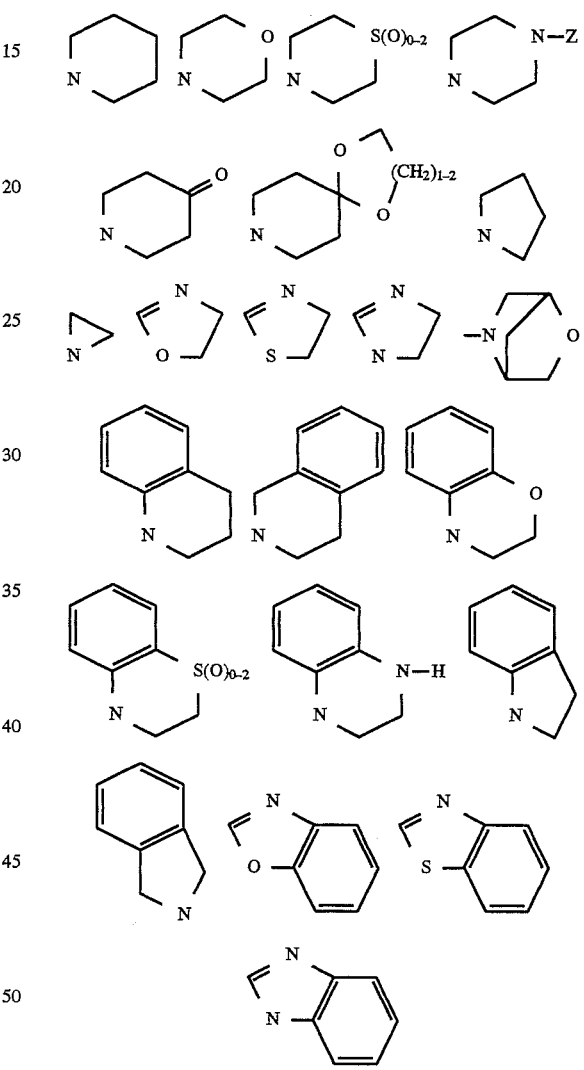

"Heteroaryl" means 5- to 6-membered aromatic rings containing a nitrogen atom and optionall containing 1 to 3 additional heteroatoms selected from the group consisting of N, S and O. The heteroaryl ring is substituted on one or more ring carbon or nitrogen atoms by a variable R² as defined above. Benzofused heteroaryl refers to radicals formed by the bonding of a benzene radical to adjacent carbon atoms on a heteroaryl ring; examples are indolyl, quinolyl, quinazolinyl, quinoxalinyl, benzotriazolyl, indazolyl, benzoxazolyl, benzothienyl and benzofuranyl. Typical heteroaryl groups are exemplified as shown:

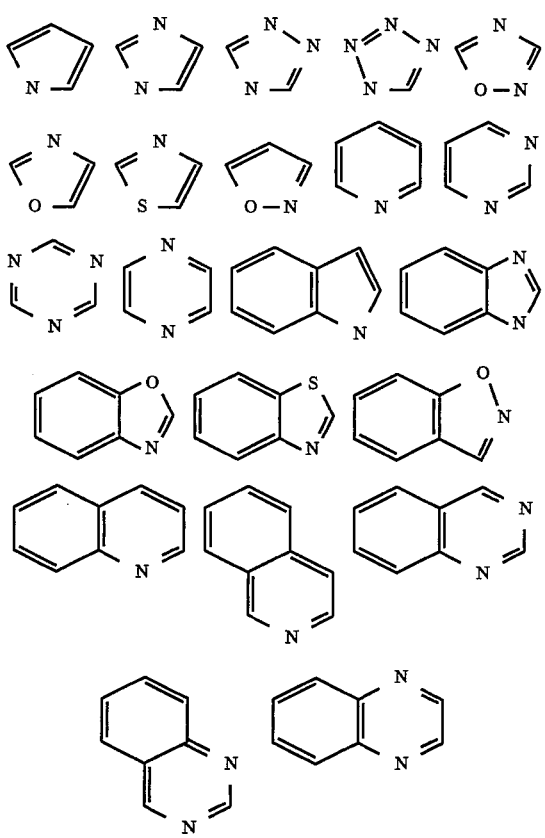

The terms heterocycloalkyl and heteroaryl include all positional isomers for a given heterocycloalkyl or heteroaryl group as defined above, for example 2-piperdinyl, 3-piperidinyl or 3-piperidinyl, and 2-pyridyl, 3-pyridyl and 4-pyridyl.

The above statements, wherein, for example, $R^{14}$, $R^{15}$ and $R^{19}$ are said to be independently selected from a group of substituents, means that $R^{14}$, $R^{15}$ and $R^{19}$ are independently selected, but also that where an $R^{14}$, $R^{15}$ or $R^{19}$ variable occurs more than once in a molecule, those occurrences are independently selected (e.g., if $R^3$ is —$OR^{14}$ wherein $R^{14}$ is hydrogen, $R^4$ can be —$OR^{14}$ wherein $R^{14}$ is lower alkyl). Those skilled in the art will recognize that the size and nature of the substituent(s) will affect the number of substituents which can be present.

Compounds of the invention have at least one asymmetrical carbon atom and therefore all isomers, including diastereomers and rotational isomers are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of formula I.

Those skilled in the art will appreciate that for some compounds of formula I, one isomer will show greater pharmacological activity than other isomers.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Cholesterol biosynthesis inhibitors for use in the combination of the present invention include HMG CoA reductase inhibitors such as lovastatin, pravastatin, fluvastatin, simvastatin and Cl-981; HMG CoA synthetase inhibitors, for example L-659,699 ((E,E-11-[3'R-(hydroxy-methyl)-4'-oxo-2'R-oxetanyl]-3,5,7R-trimethyl-2,4-undecadienoic acid); squalene synthesis inhibitors, for example squalestatin 1; and squalene epoxidase inhibitors, for example, NB-598 ((E)-N-ethyl-N-(6,6-dimethyl-2-hepten-4-ynyl)-3-[(3,3'-bithiophen-5-yl)methoxy]benzene-methanamine hydrochloride). Preferred HMG CoA reductase inhibitors are lovastatin, pravastatin and simvastatin.

Compounds of formula I can be prepared by known methods, for example WO 93/02048 describes the preparation of compounds wherein -$R^1$-Q- is alkylene, alkenylene or alkylene interrupted by a hetero atom, phenylene or cycloalkylene; WO 94/17038 describes the preparation of compounds wherein Q is a spirocyclic group; WO 95/08532, published Mar. 30, 1995 describes the preparation compounds wherein -$R^1$ -Q- is a hydroxy-substituted alkylene group; U.S. Ser. No. 08/218,498, filed Mar. 25, 1994, ABN describes compounds wherein -$R^1$-Q- is a hydroxy-substituted alkylene attached to the $Ar^1$ moiety through an —O— or $S(O)_{0-2}$— group; and U.S. Ser. No. 08/342,197, filed Nov. 18, 1994, describes the preparation of compounds wherein -$R^1$-Q- is a hydroxy-substituted alkylene group attached the the azetidinone ring by a —$S(O)_{0-2}$— group. The cited patent applications are incorporated herein by reference.

For example, compounds of formula I wherein $Ar^1$—$R^1$-Q- is phenylpropyl can be made according to the following procedures:

Method A

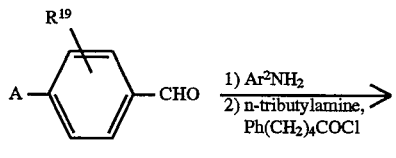

II

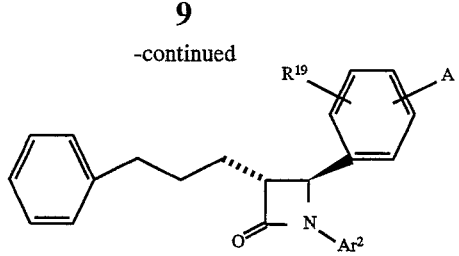

A heterocycloalkyl- or heteroaryl-substituted benzaldehyde of formula II is refluxed with an aniline derivative of formula Ar²NH₂ in an inert solvent such as toluene. n-Tributylamine is added at reflux, then 5-phenylvaleryl chloride (Ph(CH₂)₄COCl) is added and the mixture refluxed. Conventional extraction and chromatographic techniques are used to obtain the trans isomer of formula Ia.

Method B

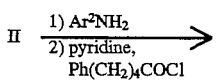

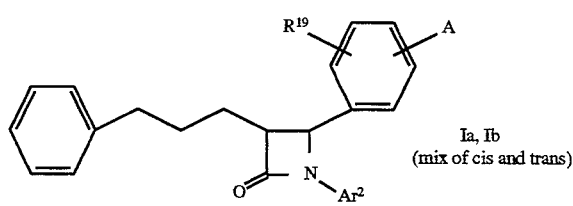

A heterocycloalkyl- or heteroaryl-substituted benzaldehyde of formula II is refluxed with an aniline derivative of formula Ar²NH₂ in an inert solvent such as toluene. Pyridine and Ph(CH₂)₄COCl are added and the mixture is refluxed, or, alternatively, the toluene is removed and pyridine serves as both the solvent and the base. Conventional extraction and chromatographic techniques are used to obtain a mixture of the cis and trans isomers of formula Ia and Ib.

Method C

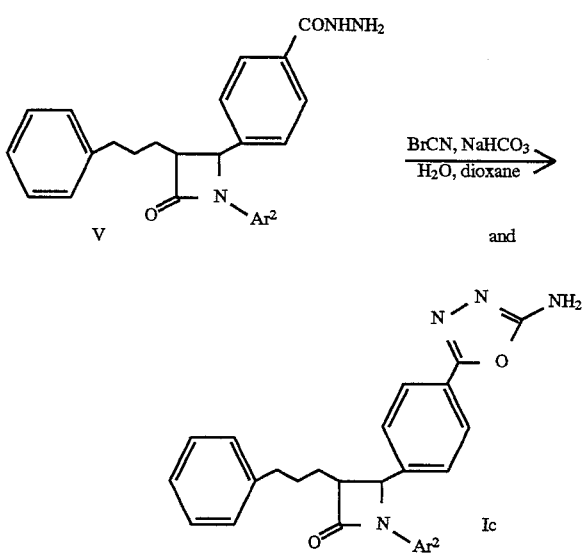

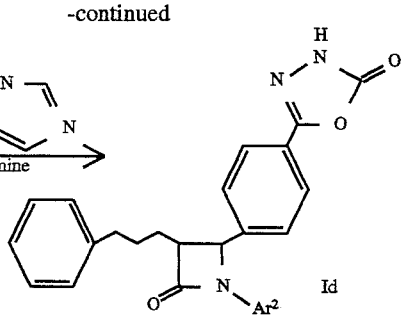

Compounds wherein $R^{19}$ is hydrogen and A is oxadiazolyl can be prepared from the corresponding benzoic acid hydrazide of formula V: an amino-substituted oxazolyl of formula Ic is prepared by reacting a mixture of the hydrazide in water and dioxane at room temperature with cyanogen bromide and NaHCO₃; a keto-substituted oxazolyl of formula Id is prepared by reacting the hydrazide with 1,1'-carbonyl diimidazole and a base such as triethylamine in an inert solvent such as tetrahydrofuran.

Method D

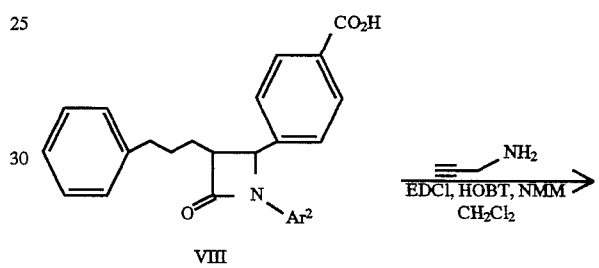

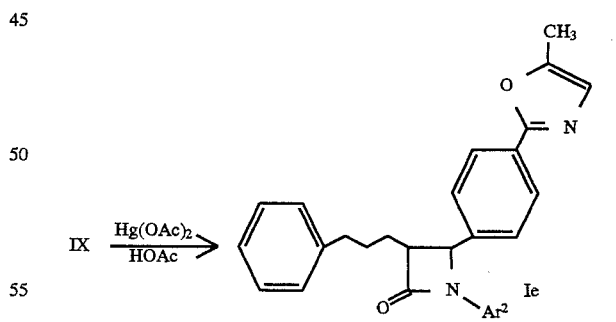

Compounds of formula I wherein A is an oxazolyl group, e.g., compounds of formula Ie, can be prepared by reacting a benzoic acid of formula VII with propargylamine in the presence of well known coupling reagents such as 1-(3-dimethylaminopropyl)-3-ethylcarbodiimide hydrochloride, hydroxybenzotriazole and N-methylmorpholine to obtain the corresponding N-3-propyne-benzamide of formula IX. The compound of formula IX is then treated with a reagent such as mercury acetate to obtain an oxazolyl-substituted compund of formula Ie.

Those skilled in the art will recognize that compounds of formula I wherein $Ar^1$—$R^1$-Q- is other than phenylpropyl can be prepared by procedures similar to Methods A–D, provided that when reactive groups are present, such as in compounds wherein a hydroxy group is present on the side chain, said reactive groups are suitable protected during the reactions.

Also, compounds of formula I wherein Q is a spiro ring can be made according to the following procedure:

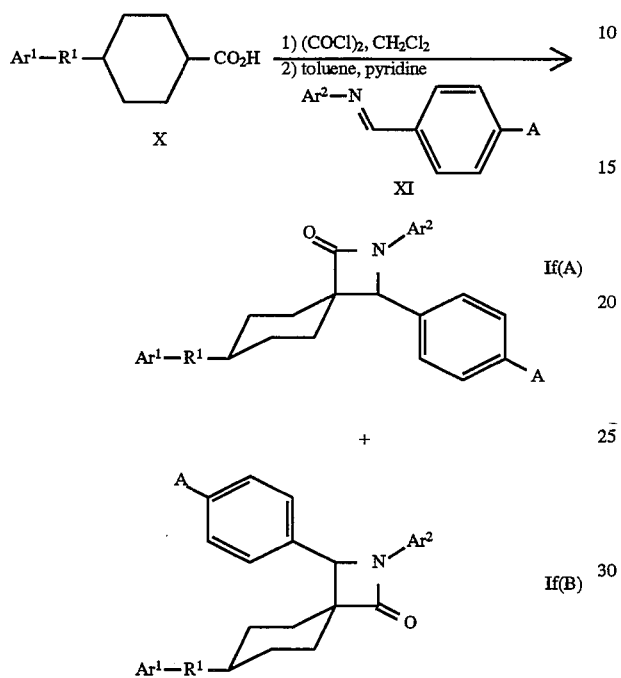

An acid of formula X can be converted to the corresponding acid chloride, and can then be reacted with an imine of formula XI by refluxing in a mixture of toluene and pyridine. The resultant crude mixture of diastereomers can be purified and separated using techniques well known in the art.

Starting materials of formula IIa, wherein A is a nitrogen-containing heterocycloalkyl or heteroaromatic group joined to the phenyl ring through a ring nitrogen, can be prepared by known methods, for example:

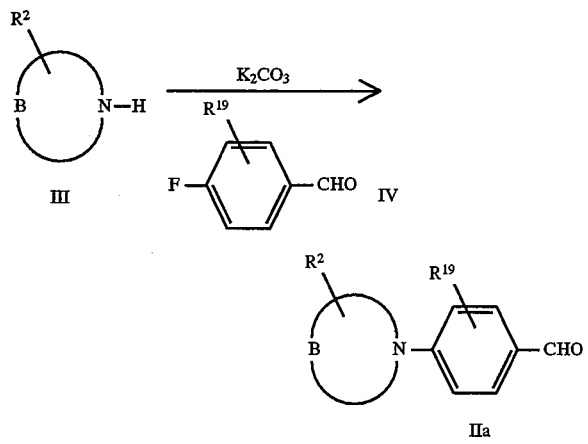

A compound of formula III, wherein B and N form a heterocycloalkane or a heteroaromatic moiety and $R^2$ is as defined above, is combined with $K_2CO_3$ (anhydrous) and heated to obtain the corresponding nitrogen-containing heterocycloalkyl- or heteroaryl-substituted benzaldehyde of formula IIa.

Starting materials of formula V can be prepared by known methods, for example:

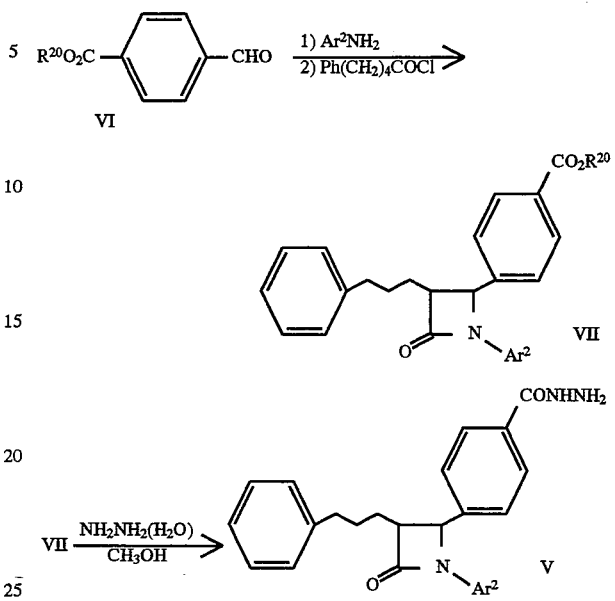

An ester of formula VI, wherein $R^{20}$ is lower alkyl, e.g., methyl, is reacted with an aniline derivative of formula $Ar^2NH_2$ followed by 5-phenylvaleryl chloride as described above in Method A to obtain the benzoate of formula VII. The benzoate is then refluxed with hydrazine hydrate to obtain a hydrazide of formula V.

Starting materials of formula VIII are prepared by deprotecting the corresponding ester of formula VII by conventional methods, e.g., by treating with a base such as LiOH or NaOH. Starting materials of formulas III, VI and X are known in the art or can be prepared by well known methods.

It will also be apparent to those skilled in the art, and by reference to the following examples, that compounds of formula I can be converted into different compounds of formula I by known methods. For example, a compound of formula I wherein A is a (4-(4-benzylpiperaziny-1-yl) group can be converted to the corresponding (4-piperazin-1-yl) compound by treatment with palladium and ammonium formate.

Reactive groups not involved in the above processes can be protected during the reactions with conventional protecting groups which can be removed by standard procedures after the reaction. The following Table 1 shows some typical protecting groups:

TABLE 1

| Group to be Protected | Group to be Protected and Protecting Group |
|---|---|
| —COOH | —COOalkyl, —COObenzyl, —COOphenyl |
| \NH/ | \NCOalkyl/, \NCObenzyl/, \NCOphenyl/ |
| | \NCH₂OCH₂CH₂Si(CH₃)₃/, \NC(O)OC(CH₃)₃/ |

TABLE 1-continued

| Group to be Protected | Group to be Protected and Protecting Group |
|---|---|
| | >N-benzyl, >NSi(CH₃)₃, >NSi—C(CH₃)₃ with CH₃ groups 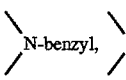 |
| —NH₂ | 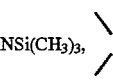 —N(succinimide-like cyclic imide) |
| —OH | —OCH₃, —OCH₂OCH₃, —OSi(CH₃)₃, —OSi—C(CH₃)₃ with CH₃ groups 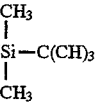 or —OCH₂phenyl |

We have found that the compounds of this invention lower serum lipid levels, in particular serum cholesterol levels. Compounds of this invention have been found to inhibit the intestinal absorbtion of cholesterol and to significantly reduce the formation of liver cholesteryl esters in animal models. Thus, compounds of this invention are hypocholesterolemic agents by virtue of their ability to inhibit the esterification and/or intestinal absorption of cholesterol; they are therefore useful in the treatment and prevention of atherosclerosis in mammals, in particular in humans.

In addition to the compound aspect, the present invention therefore also relates to a method of lowering serum cholesterol levels, which method comprises administering to a mammal in need of such treatment a hypocholesterolemic effective amount of a compound of formula I of this invention. The compound is preferably administered in a pharmaceutically acceptable carrier suitable for oral administration.

The present invention also relates to a pharmaceutical composition comprising a compound of formula I of this invention and a pharmaceutically acceptable carrier. The compounds of formula I can be administered in any conventional oral dosage form such as capsules, tablets, powders, cachets, suspensions or solutions. The formulations and pharmaceutical compositions can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like.

The daily hypocholesteremic dose of a compound of formula I is about 0.1 to about 30 mg/kg of body weight per day, preferably about 0.1 to about 15 mg/kg. For an average body weight of 70 kg, the dosage level is therefore from about 5 to about 2000 mg of drug per day, preferably about 5 to about 1000 mg, given in a single dose or 2–4 divided doses. The exact dose, however, is determined by the attending clinician and is dependent on the potency of the compound administered, the age, weight, condition and response of the patient.

For the combinations of this invention wherein the substituted azetidinone is administered in combination with a cholesterol biosynthesis inhibitor, the typical daily dose of the cholesterol biosynthesis inhibitor is 0.1 to 80 mg/kg of mammalian weight per day administered in single or divided dosages, usually once or twice a day: for example, for HMG CoA reductase inhibitors, about 10 to about 40 mg per dose is given 1 to 2 times a day, giving a total daily dose of about 10 to 80 mg per day, and for the other cholesterol biosynthesis inhibitors, about 1 to 1000 mg per dose is given 1 to 2 times a day, giving a total daily dose of about 1 mg to about 2 g per day. The exact dose of any component of the combination to be administered is determined by the attending clinician and is dependent on the potency of the compound administered, the age, weight, condition and response of the patient.

Where the components of a combination are administered separately, the number of doses of each component given per day may not necessarily be the same, e.g. where one component may have a greater duration of activity, and will therefore need to be administered less frequently.

Since the present invention relates to the reduction of plasma cholesterol levels by treatment with a combination of active ingredients wherein said active ingredients may be administered separately, the invention also relates to combining separate pharmaceutical compositions in kit form. That is, a kit is contemplated wherein two separate units are combined: a cholesterol biosynthesis inhibitor pharmaceutical composition and a substituted azetidinone absorption inhibitor pharmaceutical composition. The kit will preferably include directions for the administration of the separate components. The kit form is particularly advantageous when the separate components must be administered in different dosage forms (e.g. oral and parenteral) or are administered at different dosage intervals.

Following are examples of preparing compounds of formula I. The stereochemistry listed is relative stereochemistry unless otherwise noted. The terms cis and trans refer to the relative orientations at the β-lactam 3- and 4-positions.

PREPARATION 1

4-(4-Benzylpiperazin-1-yl)benzaldehyde

Heat a mixture of 4-benzylpiperazine (5.0 mL, 28.8 mmol), 4-flurobenzaldehyde (3.1 mL, 28.8 mmol)) and anhydrous K₂CO₃ (5.96 g, 43.1 mmol)) in DMF (50 mL) to ~150° C. overnight. Cool the mixture to room temperature, partition between water and ether (Et₂O), and extract with Et₂O. Combine the Et₂O extracts, wash with water and brine, dry over anhydrous Na₂SO₄ and concentrate in vacuo to obtain 7.91 g (98%) of 4-(4-benzylpiperazin-1-yl) benzaldehyde as a yellow solid of sufficient purity to be employed in Example 1 without further purification.

$^{1}$H NMR(400 MHz, CDCl₃): 9.77(1H, s), 7.74(2H, d, J=8.8 Hz), 7.32(5H, m), 6.90(2H, d, J=8.8 Hz), 3.58(2H, s), 3.41(4H, m), 2.61(4H, m).

PREPARATION 2

4-[1-(4-Methoxyphenyl)-3-(3-phenylpropyl)-2-oxo-4-azetidinyl]benzoic Acid Hydrazide Step 1

Reflux a solution of methyl 4-formylbenzoate (5.23 g, 31.9 mmol) and p-anisidine in toluene (50 mL) overnight with azeotropic removal of water via a Dean-Stark trap. Add n-tributylamine (22.8 mL, 95.6 mmol), followed by 5-phenylvaleryl chloride (47.8 mL, 47.8 mmol, 1M in toluene) and reflux overnight. Cool the reaction to room temperature, quench with 1M HCl and stir 15 min. Dilute the reaction mixture with ethyl acetate (EtOAc), wash with 1M HCl, water and brine, dry over Na₂SO₄ and concentrate. Dissolve the resulting residue in tetrahydrofuran (THF), dilute with an equal volume of CH₃OH, add NaBH₄ (1.22 g, 32 mmol) and stir for 30 min. Add 1M HCl, dilute with EtOAc and wash with 1M HCl, water and brine. Dry over $Na_2SO_4$, filter and concentrate on enough silica gel to obtain a free-flowing powder. Load the powder onto a chromatography column packed with silica and 30% EtOAc/hexanes and elute with the same solvent to obtain 12.2 g (92%) of methyl 4-[1-(4-methoxyphenyl)-3-(3-phenylpropyl)-2-oxo-4-azetidinyl]benzoate as a 12/1 trans/cis mixture. $^1$H NMR (400 MHz, $CDCl_3$, trans isomer) 8.05(2H, d; J=8.2 Hz), 7.39(2H, d, J=8.2 Hz), 7.28(3H, m), 7.17(6H, m), 6.77(2H, d, J=6.9 Hz), 4.65(1H, d, J=2.1 Hz), 3.91(3H, s), 3.73(3H, s), 3.09(1H, m), 2.65(2H, m), 1.97(1H, m), 1.82(3H, m). Diagnostic C-4 proton for cis diastereomer 5.18(J=5.7 Hz). MS(EI): 429($M^+$,6), 269(13), 149(100).

Step 2

Reflux a mixture of the product of Step 1 (7.5 g, 17.5 mmol, 12/1 trans/cis mixture) and hydrazine hydrate (4.7 mL, 87.3 mmol) in $CH_3OH$ (40 mL) overnight, monitoring the reaction by TLC (30% EtOAc/hexanes) and adding additional hydrazine and refluxing further as necessary. Evaporate most of the solvent in vacuo and partition the resultant residue between water and EtOAc. Wash with water and brine, dry over $Na_2SO_4$ and concentrate onto silica gel to obtain a free-flowing powder. Load the powder onto a chromatography column packed with silica and EtOAc. Elute with EtOAc to obtain 3.8 g (50%) of the title compound as a 6/1 trans/cis mixture. $^1$H NMR (400 MHz, $CDCl_3$, trans isomer) 7.74(2H, d, J=8.2 Hz), 7.39(2H, d, J=8.2 Hz), 7.28(2H, m), 7.16(5H, m), 6.76(2H, d, J=9.1 Hz), 4.63(1H, d, J=2.1 Hz), 3.73(3H, s), 3.06(1H, m), 2.65(2H, m), 1.98(1H, m), 1.85(3H, m). Diagnostic C-4 proton for cis diastereomer 5.16(J=5.6 Hz). MS(EI): 429($M^+$,74), 249 (100), 149(35). HRMS calculated for $C_{26}H_{27}N_3O_3$: 429.2052; found 429.2052.

PREPARATION 3

4-[1-(4-Methoxyphenyl)-3-(3-phenylpropyl)-2-oxo-4-azetidinyl]benzoic Acid

Add 2N NaOH (39 mL, 78 mmol) to a room temperature solution of the product of Preparation 2, Step 1 (6.7 g, 15.6 mmol, 12/1 ranc/cis mixture) in 50% THF/$CH_3OH$ (200 mL). Stir the mixture overnight, evaporate most of the solvent in vacuo and partition the residue between 3N HCl and EtOAc. Extract with EtOAc, combine the extracts, wash with water and brine, dry over $Na_2SO_4$ and concentrate to obtain 6.87 g (approx. 100%) of the title compound as a 11/1 trans/cis mixture. $^1$H NMR (300 MHz, $CDCl_3$, trans isomer) 8.17 (2H, d, J=8.3 Hz), 7.50(2H, d, J=8.3 Hz), 7.35(3H, m), 7.25(4H, m), 6.85(2H, d, J=9.0 Hz), 4.74(1H, d, J=2.2 Hz), 3.81(3H, s), 3.13(1H, m), 2.73(2H, m), 1.92(4H, m). Diagnostic C-4 proton for cis diastereomer 5.27(J=5.7 Hz). Elemental analysis for $C_{26}H_{25}NO_4$: calculated C=75.15, H=6.06, N=3.37; found C=74.79, H=6.18, N=3.58.

EXAMPLE 1 trans-1-(4-Methoxyphenyl)-3-(3-phenylpropyl)-4-[4-(4-benzylpiperazin-1-yl)phenyl]-2-azetidinone Reflux a solution of the product of Preparation 1 (7.89 g, 28.1 mmol) and 4-methoxyaniline (3.47 g, 28.1 mmol) in toluene (100 mL) with azeotropic removal of water via a Dean-Stark trap. Monitor the progress of the reaction by NMR. When the reaction is complete, add n-tributylamine (20.1 mL, 84.4 mmol) at reflux, then add 5-phenylvaleryl chloride (42.2 mL, 42.2 mmol, 1M in toluene) and reflux the mixture overnight. Again, monitor the progress of the reaction by NMR, and if it indicates that a considerable amount of imine remains, add addtional 5-phenylvaleryl chloride (1.5–2.0 eq, 1M in toluene) and n-tributylamine (2.2–3.0 eq) and continue to reflux; repeat this process as needed until no further reaction progress is evident by NMR. Cool the mixture to room temperature, partition between $NH_4Cl$ (sat.) and EtOAc, and extract with EtOAc. Combine the extracts, wash with $NH_4Cl$ (sat.), water and brine, dry over anhydrous $Na_2SO_4$ and concentrate to a brown oil. Chromatograph on silica gel, eluting with 33% EtOAc/hexanes, to obtain 4.14 g (27%) of an amber oil. Recrystallize from EtOAc/hexanes to obtain 0.67 g of the title compound. M.p. 139°–140° C.; $^1$H NMR: (400MHz, $CDCl_3$): 7.33(4H, m), 7.26(4H, m), 7.17(6H, m), 6.87(2H, d, J=8.6 Hz), 6.75(2H, d, J=8.9 Hz), 4.51(1H, d, J=2.12 Hz), 3.72(3H, s), 3.58(2H, m), 3.21(4H, s), 3.07(1H, m), 2.61(6H, m), 1.94(1H, m), 1.82(3H, m); MS: (CI): 546 ($M^+$, 47), 397(24), 150(100), 91(33).

Using appropriate starting materials in a procedure similar to that described above, compounds shown in the following table can be prepared, wherein A and Ar are as defined in the table:

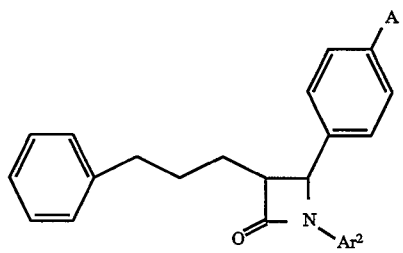

| Ex. # | A | $Ar^2$ | M.p., °C. | NMR | HRMS | MS |
|---|---|---|---|---|---|---|
| 1A | —N\_\_\_NCH$_3$ | 4-PhOMe | 106–107 | — | $C_{30}H_{35}N_3O_2$ calc'd: 469.2729 found: 469.2711 | (EI): 469($M^+$, 1), 320(100), 215(36), 149(19), 91(41) |

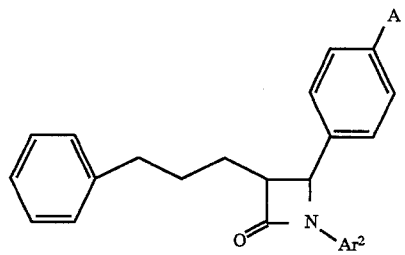

| Ex. # | A | Ar² | M.p., °C. | NMR | HRMS | MS |
|---|---|---|---|---|---|---|
| 1B | piperazinyl-C₆H₄-OCH₃ (4-methoxyphenyl-piperazine) | Ph | 282–283 | (400MHz, CDCl₃): 7.22(13H, m), 7.03(1H, m), 6.95(2H, d, J=8.4Hz), 6.91(2H, d, J=9.0Hz), 4.58(1H, d, J=2.12Hz), 3.78(3H, s), 3.51(4H, m), 3.22(4H, m), 3.08(1H, m), 2.65(2H, m), 1.97(1H, m), 1.85(3H, m) | $C_{35}H_{37}N_3O_2$ calc'd: 531.2886 found: 531.2906 | (EI): 531(M⁺, 63), 412(100), 119(24) |
| 1C | cyclohexyl-piperazine | Ph | 179 | (400MHz, CDCl₃): 7.21(11H, m), 7.14(1H, m), 6.89(2H, d, J=8.8Hz), 4.56(1H, d, J=2.2Hz), 3.21(4H, m), 3.08(1H, m), 2.72(4H, m), 2.64 (2H, m), 2.31(1H, m), 1.93(3H, m), 1.82(5H, m), 1.61(2H, m), 1.25(3H, m), 1.15(1H, m) | — | (CI): 508(M⁺, 100), 389(33), 120(90) |
| 1D | 4-(dimethylamino)piperidine | 4-PhOMe | 103–104 | — | $C_{32}H_{39}N_3O_2$ calc'd: 497.3042 found: 497.3066 | (EI): 497(M⁺, 13), 348(83), 303(100), 198(28) |
| 1E | piperazinyl-CH₂-C(O)-morpholine | 4-PhOMe | 167.5–168 | 400MHz, CDCl₃: 7.21(9H, m), 6.88(2H, d, J=8.6Hz), 6.75(2H, d, J=9.0Hz), 4.52(1H, d, J=2.2Hz), 3.73(3H, s), 3.66(8H, m), 3.22(6H, m), 3.06(1H, m), 2.67(6H, s), 1.96(1H, m), 1.82(3H, m) | $C_{35}H_{42}N_4O_4$ calc'd: 583.3278 found: 583.3284 | (EI): 583(M⁺, 34), 307(36), 289(16), 238(25) |
| 1F | bicyclic N-O (8-oxa-3-azabicyclo) | Ph | — | 400MHz, CDCl₃: 7.23(11H, m), 7.02(1H, m), 6.55(2H, d, J=8.6Hz), 4.65(1H, s), 4.55(1H, d, J=2.2Hz), 4.39(1H, d, J=4.9Hz), 3.88(2H, m), 3.54(1H, m), 3.16(1H, m), 3.10(1H, m), 2.65(2H, m), 1.98(3H, m), 1.84(3H, m) | $C_{29}H_{30}N_2O_2$ calc'd: 438.2307 found: 438.2316 | (EI): 438(M⁺, 23), 319(100), 289(28), 248(23), 58(100) |

EXAMPLE 2

4-(4-(Morpholin-1-yl)phenyl)-3-(3-phenylpropyl)-1-(4-methoxyphenyl)-2-azetidone Reflux a solution of 4-(morpholin-1-yl)benzaldehyde (8.94 g, 46.8 mmol) and 4-methoxyaniline (5.76 g, 46.8 mmol) in toluene (250 mL) with azeotropic removal of water via a Dean-Stark trap for 10 h and cool to room temperature. Collect the resultant precipitate via vacuum filtration, wash with hexanes and dry under vacuum to give 10.2 g (74%) of N-[4-(morpholin-1-yl)benzidene]-4-methoxyaniline. Dissolve the product in toluene (75 mL). Add pyridine (1.43 mL, 17.5 mmol) followed by 5-phenylvaleryl chloride (15.2 mL, 15.2 mmol, 1M in toluene) at room temperature. Warm the mixture to reflux, and reflux overnight. Monitor the progress of the reaction as described in Example 1. Cool the mixture to room temperature, diluted with EtOAc and wash with 0.1M NaOH, 1M HCl, water and brine, dry over anhydrous Na₂SO₄ and concentrate. Chromatograph the residue on silica gel, eluting with 40% EtOAc/hexanes to obtain 2.71 g (77%) of the title compound as a 1/1 mixture of cis and trans isomers. Additional chromatography provides pure cis and trans isomers:

2A) trans isomer: ¹H NMR (200 MHz, CDCl₃): 7.20(9H, m), 6.92(2H, d, J=8.7 Hz), 6.76(2H, d, J=9.0 Hz), 4.54( 1H, d, J=2.2 Hz), 3.87(4H, m), 3.73(3H, s), 3.17(4H, m), 3.07 (1H, m), 2.64(2H, m), 1.83(4H, m); HRMS: $C_{29}H_{32}N_2O_3$ calc. 456.2413, obsvd. 456.2426; MS: (Cl):457(M⁺, 100), 307(27), 150(47).

2B) cis isomer: ¹H NMR (200 MHz, CDCl₃): 7.21(7H, m), 6.91 (4H, m), 6.77(2H, d, J=9.1 Hz), 5.08(1H, d, J=5.6 Hz), 3.88(4H, m), 3.74(3H, s), 3.52(1H, m), 3.35(1H, m), 3.20(3H, m), 2.41(2H, m), 1.61 (2H,m), 1.26(2H, m); HRMS: $C_{29}H_{32}N_2O_2$ calc. 456.2413, obsvd. 456.2420.

Using appropriate starting materials in a procedure similar to that described above, compounds shown in the following table can be prepared, wherein A and Ar are as defined in the table:

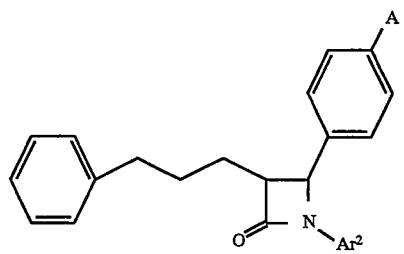

| Ex. # | A | Ar² | M.p., °C. | NMR | HRMS | MS |
|---|---|---|---|---|---|---|
| 2C | —N(piperidinyl) | 4-PhOMe | 110–111 | (400MHz, CDCl₃): 7.23(4H, m), 7.13(3H, m) 7.02(2H, d, J=1.2Hz), 6.89(2H, m), 6.77(2H, d, J=9.1Hz), 5.07(1H, d, J=5.5Hz), 3.74(3H, s), 3.50(1H, m), 3.18(4H, m), 2.43(2H, m), 1.72(4H, m), 1.60(4H, m), 1.43(1H, m), 1.31(1H, m) | — | (EI): 454(M⁺, 1), 305(100), 200(67), 91(12) |
| 2D | —N(piperidinyl) | 4-PhOMe | 95–96 | (300MHz, CDCl₃): 7.21(9H, m), 6.89(2H, d, J=8.7Hz), 6.75(2H, d, J=9.0Hz), 4.51(1H, d, J=2.3Hz), 3.73(3H, s), 3.15(4H, m), 3.07(1H, m), 2.62(2H, m), 1.83(2H, m), 1.68(4H, m), 1.59(4H, m) | $C_{30}H_{34}N_2O_2$ calc'd: 454.2620 found: 454.2642 | (EI): 454(M⁺, 1), 305(100), 200(87), 91(22) |
| 2E | —N(thiomorpholinyl) | 4-PhOMe | 111–112 | 400MHz, CDCl₃): 7.20(9H, m), 7.01(2H, d, J=7.3Hz), 6.78(2H, d, J=8.9Hz), 5.07(1H, d, J=5.7Hz), 3.75(3H, s), 3.63(4H, m), 2.44(2H, m), 1.67(1H, m), 1.49(7H, m), 1.19(1H, m) | $C_{29}H_{32}N_2O_2S$ calc'd: 472.2185 found: 472.2174 | (CI): 473(M⁺, 75), 284(37), 253(39), 119(100), 107(55) |
| 2F | —N(thiomorpholinyl) | 4-PhOMe | — | (400MHz, CDCl₃): 7.21(9H, m), 6.89(2H, m), 6.77(2H, d, J=8.7Hz), 4.53(1H, d, J=2.1Hz), 3.73(3H, s), 3.56(4H, m), 3.07(1H, m), 2.74(4H, m), 2.65(2H, m), 1.98(1H, m), 1.85(3H, m) | — | (CI): 473(M⁺, 100), 323(26), 150(24) |
| 2G | —N(dioxaspiro) | 4-PhOMe | 143–143.5 | (400MHz, CDCl₃): 7.22(4H, m), 7.14(3H, m), 7.00(2H, d, J=7.3Hz) 6.90(2H, m), 6.78(2H, d, J=9.1Hz), 5.07(1H, d, J=5.7Hz)), 4.00(4H, s), 3.74(3H, s), 3.50(1H, m), 3.36(4H, m), 2.42(2H, m), 1.85(4H, m), 1.56(4H, s) | — | (CI): 513(M⁺, 100), 363(28), 294(10), 150(14) |
| 2H | —N(dioxaspiro) | 4-PhOMe | 119.5–120 | (300MHz, CDCl₃): 7.21(9H, m), 6.89(2H, m) 6.76(2H, d, J=8.9Hz), 4.52(1H, bs), 3.99(4H, s), 3.73(3H, s), 3.36(4H, m), 3.05(1H, m), 2.64(2H, m), 1.82(4H, m), 1.56(4H, s) | — | (CI): 513(M⁺, 100), 363(34), 294(14), 248(20), 150(53) |
| 2I | —N(piperazinyl)NCH₃ | Ph | 110–111 | (400MHz, CDCl₃): 7.25(6H, m), 7.14(3H, m), 6.95(3H, m), 6.88(2H, d, J=8.8Hz), 5.11(1H, d, J=5.8Hz), 3.51(1H, m), 2.56(4H, m), 3.26(4H, m), 2.45(1H, m), 2.39(4H, m), 1.61(3H, m), 1.44(1H, m) | — | (EI): 439(M⁺, 5), 320(62), 215(29), 91(48), 70(100) |
| 2J | —N(piperazinyl)N | Ph | 140–141 | (400MHz, CDCl₃): 7.23(11H, m), 7.03(1H, m), 6.90(2H, d, J=8.8Hz), 4.58(1H, d, J=2.2Hz), 3.24(4H, m), 3.08(1H, m), 2.64(2H, m), 2.57(4H, m), 2.36(3H, s), 1.98(1H, m), 1.84(3H, m) | — | (EI): 439(M⁺, 3), 320(56), 215(34), 119(42), 91(78), 70(100) |

EXAMPLE 3

1-(4-Methoxyphenyl)-(3-phenylpropyl)-4-(Imidazoyl-1-yl)phenyl-2-azetidone

Heat a mixture of 4-(1-imidazoyl)benzyaldehyde (3.79 g, 22 mmol) and 4-methoxyaniline (2.71 g, 22 mmol) in $CH_3OH$ (200 mL) to reflux for a short time. Allow the solution to cool to room temperature and stand overnight. Collect the resultant precipitate by vacuum filtration and dry to obtain 6.1 g (100%) of N-[4-(imidazoyl-1-yl)benzidene]-4-methoxyaniline. Treat the product with pyridine, n-tributylamine and 5-phenylvaleryl chloride in the manner described in Example 2, then extract and chromatograph in a manner similar to Example 2 obtain the title compound as a cis/trans ratio of 1/1.17. $^1$H RMS: $C_{28}H_{27}N_3O_2$ calc. 437.2103, obsvd. 437.2096; MS: (CI): 438($M^+$, 86), 289 (67), 161(38), 150(100).

EXAMPLE 4

4-[4-(2-Pyrimidyl)piperazin-1-yl]phenyl)-3-(3-phenylpropyl)-1-(4-methoxyphenyl)-2-azetidone Reflux a mixture of [4-(2-pyrimidyl)piperazinyl]benzaldehyde (5.62 g, 21 mmol) and 4-methoxyaniline (2.58 g, 21 mmol) in toluene (250 mL) with azeotropic removal of water via a Dean-Stark trap. Monitor progress of the reaction by $^1$H NMR. After 3 days, at 85% completion, cool the mixture to room temperature, concentrate and recrystallize the residue from EtOAc and hexanes to obtain 6.6 g (85%) of N-[4-(morpholin-1-yl)benzidene]-4-methoxyaniline as a yellow solid. Dissolve the product in pyridine (80 mL), add 5-phenylvaleryl chloride (11 mL, 11 mmol, 1M in toluene) at room temperature and reflux overnight. Monitor the reaction as described in previous examples. Remove most of the pyridine by distillation, cool the solution to room temperature, partition between EtOAc and water, wash with water and brine, concentrate and chromatograph on silica gel to provide 1.02 g (36%) of the title compound as a 1/1 cis/trans mixture. Additional silica gel chromatography provides pure cis and trans isomers:

4A: $^1$H NMR (400 MHz, $CDCl_3$): pertinent signals: 5.08 and 4.54 (1H, d, $J_1$=5.7 Hz, cis, $J_2$=2.1 Hz, trans C-4); MS: (CI): 534($M^+$, 18), 385(17), 150(100), 125(35), 91(58).

4B: M.p. 126°–127° C.; (400 MHz, $CDCl_3$): 8.34(2H, d, J=4.6 Hz, 7.21(9H, m), 6.93(2H, d, J=8.6 Hz), 6.76(2H, d, J=8.6 Hz), 6.53(1H, t, J=4.8 Hz), 4.54(1H, d, J=2.2 Hz), 3.97(4H, m), 3.73(3H, s), 3.26(4H, m), 3.07(1H, m), 2.64 (2H, m), 1.97(1H, m), 1.83(3H, m); (CI): 534($M^+$, 33), 384(26), 150(100), 124(16), 91(29).

EXAMPLE 5 trans-1-(4-Methoxyphenyl)-3-(3-phenylpropyl)-4-(4-piperazin-1-yl)phenyl-2-azetidinone Add ammonium formate (3.0 g, 48 mmol) to a refluxing suspension of the product of Example 1 (3.0 g, 5.53 mmol) and 10% Pd/C (0.7 g) in $CH_3OH$ (20 mL). React for 4 h, monitoring reaction progress by TLC (eluting with 30% EtOAc/hexanes). Filter the reaction mixture through celite and wash the filter cake well with $CH_3OH$. Concentrate the filtrate and partition the resulting residue between brine and EtOAc, and extract with EtOAc. Combine the extracts, wash with brine, dry over anhydrous $Na_2SO_4$ and concentrate. Chromatograph the resulting residue on silica gel, eluting with 10% $MeOH/CH_2Cl_2$ to obtain a crude product. Recrystallize to obtain the pure title compound. M.p. 204°–206° C.; $^1$H NMR (400 MHz, $CDCl_3$): 7.33(4H, m), 7.26(4H, m), 7.17(5H, m), 6.89(2H, d, J=8.6 Hz), 6.77(2H, d, J=9.0 Hz), 4.54(1H, d, J=2.1 Hz), 3.73(3H, s), 3.50(4H, m), 3.37(4H, m), 3.05(1H, m), 2.64(2H, m), 1.95(1H, m), 1.84(3H, m); MS: (CI): 456($M^+$, 100), 306(25), 150(17).

EXAMPLE 6

5-[4-[1-(4-Methoxyphenyl)-3-(3-phenylpropyl)-2-oxo-4-azetidinyl]] 1,3,4-Oxadiazol-2-amine Stir a mixture of the product of Preparation 2 (0.59 g, 1.36 mmol, 6/1 trans mixture), $NaHCO_3$ (0.12 g, 1.42 mmol), water (2.5 mL) and dioxane (3.5 mL) for 5 min. at room temperature. Add BrCN (0.15 g, 1.42 mmol), stir for 4 h., and filter. Wash the filter cake with water and dry in vacuo overnight to obtain 0.50 g (81%) of the title compound as a 8/1 trans/cis mixture. M.p. 207°–210° C. $^1$H NMR (400 MHz, $CDCl_3$, trans isomer) 7.90(2H, d, J=8.5 Hz), 7.42(2H, d, J=8.3 Hz), 7.28(3H, m), 7.17(4H, m), 6.77(2H, d, J=9.1 Hz), 5.56(2H, bs), 4.64(1H, d, J=2.2 Hz), 3.73(3H, s), 3.10(1H, m), 2.66(2H, m), 1.97(1H, m), 1.85(3H, m). Diagnostic C-4 proton for cis diastereomer 5.17(J=5.6 Hz). MS(EI): 454($M^+$,55), 362(46), 305(100), 149(94). HRMS calculated for $C_{26}H_{26}N_4O_3$: 454.2005; found 454.2012.

EXAMPLE 7

5-[4-[1-(4-Methoxyphenyl)-3-(3-phenylpropyl)-2-oxo-4-azetidinyl]phenyl]-1,3,4-oxadiazol-2(3H)-one Add 1,1'-carbonyl diimidazole (0.22 g, 1.36 mmol) to a 0° C. solution of the product of Preparation 2 (0.39 g, 0.91 mmol, 6/1 trans/cis mixture) and triethylamine (0.25 mL, 1.82 mmol) in THF (5 mL) and allow the mixture to warm to room temperature overnight. Concentrate the mixture in vacuo and dissolve the residue in EtOAc. Wash with 1M HCl, saturated $NaHCO_3$, water and brine, dry over $Na_2SO_4$ and concentrate on silica to obtain a free-flowing powder. Load the powder onto a chromatography column packed with silica gel and 40% EtOAc/hexanes and eluts with the same solvent to obtain 0.383 g (93%) of the title compound as a 9/1 trans/cis mixture. $^1$H NMR (400 MHz, $CDCl_3$, trans isomer) 7.85(2H, d, J=7.9 Hz), 7.44(2H, d, J=7.9 Hz), 7.27(2H, m), 7.17(5H, m), 6.78(2H, d, J=8.8 Hz), 4.66(1H, s), 3.73(3H, s), 3.10(1H, m), 2.66(2H, m), 1.99(1H, m), 1.86(3H, m). Diagnostic C-4 proton for cis diastereomer 5.18(J=5.4 Hz). MS(EI): 455($M^+$,94), 306(49), 295(81 ), 149(100). HRMS calculated for $C_{27}H_{25}N_3O_4$: 455.1845; found 455.1849.

EXAMPLE 8

2-[4-[1-(4-Methoxyphenyl)-3-(3-phenylpropyl)-2-oxo-4-azetidinyl]phenyl]-4-methyloxazole Step 1

Add 1-(3-dimethylaminopropyl)-3-ethylcarbodiimide hydrochloride (0.89 g, 4.64 mmol) to a room temperature solution of the product of Preparation 3 (1.61 g, 3.86 mmol, 11/1 trans/cis mixture), propargylamine (0.318 mL, 4.64 mmol), hydroxybenzotriazole (0.625 g, 4.64 mmol), and N-methylmorpholine (0.85 mL, 7.72 mmol) in $CH_2Cl_2$ (15 mL) and stir overnight. Dilute the mixture with $CH_2Cl_2$, wash with water, dry over $Na_2SO_4$ and concentrate onto silica. Load the silica onto a chromatography column packed with silica and 50% EtOAc/hexanes. Elute with the same solvent to obtain 1.24 g (71%) of N-3-propyne-4-[1-(4-methoxyphenyl)-3-(3-phenylpropyl)-2-oxo-4-azetidinyl]

benzamide as a 12/1 trans/cis mixture. MS (Cl): 453($M^{+1}$, 100), 304(57), 150(92).

Step 2

Combine the product of Step 1 (1.21 g, 2.67 mmol, 12/1 trans/cis mixture) and mercury acetate (0.05 g, 0.16 mmol) in acetic acid (10 mL) and reflux for 3 h. Cool the reaction mixture to room temperature and concentrate in vacuo. Partition the resultant residue between saturated $K_2CO_3$ and EtOAc, then extract with EtOAc. Combine the extracts, wash with water and brine, then dry over $Na_2SO_4$ and concentrate onto silica. Load the silica onto a chromatography column packed with silica and 30% EtOAc/hexanes. Elute with 30–40% EtOAc/hexanes to obtain 0.74 g (61%) of the title compound as a 6/1 trans/cis mixture. $^1$H NMR (400 MHz, $CDCl_3$, trans isomer) 7.99(2H, d, J=8.4 Hz), 7.40(2H, d, J=8.5 Hz), 7.28(2H, m), 7.18(5H, m), 6.83(1H, d, J=1.2 Hz), 6.77(2H, d, J=9.0 Hz), 4.63(1H, d, J=2.2 Hz), 3.73(3H, s), 3.12(1H, m), 2.66(2H, m), 2.39(3H, s), 1.99 (1H, m), 1.86(3H, m). Diagnostic C-4 proton for cis diastereomer 5.16(J=5.5 Hz). MS(EI): 452($M^+$,48), 303(100), 198(26). HRMS calculated for $C_{29}H28N_2O_4$: 452.2100; found 452.2089.

EXAMPLE 9

3-[4-(4-Methyl-1-piperazinyl)phenyl]-2,7-diphenyl-2-azaspiro[5.3]nonan-1-one

Add oxalyl chloride (0.8 mL, 9.46 mmol) to a refluxing solution of 4-phenylcyclohexanecarboxylic acid in $CH_2Cl_2$ (10 mL). After 2 h, cool to room temperature and evaporate the solvent in vacuo. Dissolve the resultant residue in toluene, add to a refluxing solution of N-4-[4-methyl-1-piperazinyl]benzylideneaniline (1.2 g, 4.3 mmol) in a mixture of toluene (15 mL) and pyridine (5 mL), and reflux overnight. Pour the reaction mixture into water, extract with $CH_2Cl_2$, combine the extracts and evaporate the solvent. Chromatograph the resultant residue on silica, eluting with 10% $CH_3OH/CH_2Cl_2$ to obtain crude title compound as a mixture of diastereomers. Purify the mixture by preparative silica TLC, eluting twice with 10% $CH_3OH/EtOAc$ to obtain the title compound as a mixture of diastereomers. Separate the diastereomers by preparative silica TLC, eluting three times with 10% $CH_3OH/EtOAc$ to obtain diastereomers A and B with a combined yield of 0.19 g (9%).

Diastereomer A: M.p. 215°–217° C. HRMS: calculated for $C_{31}H_{36}N_3O$ ($M^{+1}$): 466.2858; found 466.2861. $^1$H NMR (400 MHz, $CDCl_3$) 7.21 (11H, m), 7.03(1H, m), 6.93(2H, d, J=8.8 Hz), 4.88(1H, s), 3.25(3H, m), 2.63(3H, m), 2.52(2H, m), 2.38(3H, s), 2.13(3H, m), 2.1–1.8(5H, m), 0.89(1H, m).

Diastereomer B: M.p. 166°–168°C.. HRMS: calculated for $C_{31}H_{36}N_3O$ ($M^{+1}$): 466.2858; found 466.2857. $^1$H NMR (400 MHz, $CDCl_3$) 7.24(9H, m), 7.12(2H, d, J=8.6 Hz), 7.04(1H, m), 6.90(2H, d, J=8.6 Hz), 4.67(1H, s), 3.27(4H, bs), 2.64(4H, bs), 2.41 (4H, m), 2.8–1.7(7H, m), 0.98(1H, m).

The following formulations exemplify some of the dosage forms of this invention. In each, the term "active compound" designates a compound of formula I.

EXAMPLE A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
| | Total | 300 | 700 |

Method of Manufacture

Mix Item Nos. 1 and 2 in suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

EXAMPLE B

Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
| | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

Representative formulations comprising a cholesterol biosynthesis inhibitor are well known in the art. It is contemplated that where the two active ingredients are administered as a single composition, the dosage forms disclosed above for substituted azetidinone compounds may readily be modified using the knowledge of one skilled in the art.

The in vivo activity of the compounds of formula I can be determined by the following procedure.

In Vivo Assay of Hypolipidemic Agents Using the Hyperlipidemic Hamster

Hamsters are separated into groups of six and given a controlled cholesterol diet (Purina Chow #5001 containing 0.5% cholesterol) for seven days. Diet consumption is monitored to determine dietary cholesterol exposure in the presence of test compounds. The animals are dosed with the test compound once daily beginning with the initiation of diet. Dosing is by oral gavage of 0.2 mL of corn oil alone (control group) or solution (or suspension) of test compound in corn oil. All animals moribund or in poor physical condition are euthanized. After seven days, the animals are anesthetized by IM injection of ketamine and sacrificed by decapitation. Blood is collected into vacutainer tubes containing EDTA for plasma lipid analysis and the liver excised for tissue lipid analysis. Data is reported as percent reduction of lipid versus control.

Using the hamster in vivo test procedures substantially as described above, the following data were obtained. Compounds are referred to in the following table by the corresponding example numbers. Data is reported as percent change versus control, therefore, negative numbers indicate a positive lipid-lowering effect.

|  | % Reduction | | |
|---|---|---|---|
| Ex. # | Serum Cholest. | Cholest. Esters | Dose mg/kg |
| 1 | −11 | 0 | 50 |
| 1A | −22 | −96 | 50 |
| 1B | 0 | −22 | 50 |
| 1C | −15 | −27 | 50 |
| 1D | 0 | 0 | 50 |
| 1E | — | −28 | 50 |
| 1F | −17 | −81 | 50 |
| 2A | −37 | −81 | 50 |
| 2B | −39 | −87 | 50 |
| 2C | −45 | −64 | 50 |
| 2D | −13 | −54 | 50 |
| 2E | −20 | −87 | 50 |
| 2F | 0 | −23 | 50 |
| 2G | 0 | −21 | 50 |
| 2H | 0 | −15 | 50 |
| 2I | −18 | −39 | 50 |
| 2J | −25 | −65 | 50 |
| 3 | 0 | 0 | 50 |
| 4A | −11 | 0 | 50 |
| 4B | 0 | 0 | 50 |
| 5 | 0 | −22 | 50 |
| 6 | 0 | 0 | 50 |
| 7 | −16 | −32 | 50 |
| 8 | 0 | −24 | 50 |
| 9A | +20 | +19 | 10 |
| 9B | 0 | −31 | 10 |

We claim:

1. A compound selected from the group of compounds represented by the formula:

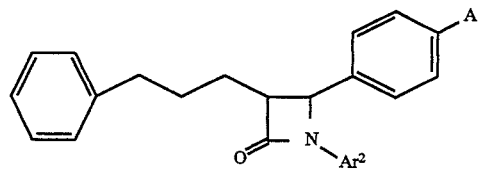

wherein A and Ar$^2$, and cis and trans isomers are as defined in the following table:

| A | Ar$^2$ | Relative Stereochemistry |
|---|---|---|
| −N⟨piperazine⟩N—CH$_2$C$_6$H$_5$ | 4-(CH$_3$O)—C$_6$H$_4$— | trans |
| −N⟨piperazine⟩NCH$_3$ | 4-(CH$_3$O)—C$_6$H$_4$— | trans |
| −N⟨piperazine⟩N—C$_6$H$_4$—OCH$_3$ | C$_6$H$_5$— | trans |
| −N⟨piperazine⟩N—cyclohexyl | C$_6$H$_5$— | trans |
| −N⟨piperazine⟩N—CH$_2$C(O)N⟨morpholine⟩ | 4-(CH$_3$O)—C$_6$H$_4$— | trans |
| −N⟨bicyclic with O⟩ | C$_6$H$_5$— | trans |

| [A] | [Ar$^2$] | [Relative Stereochemistry] |
|---|---|---|
| −N⟨morpholine⟩ | 4-(CH$_3$O)—C$_6$H$_4$— | trans |
| −N⟨morpholine⟩ | 4-(CH$_3$O)—C$_6$H$_4$— | cis |
| −N⟨piperidine⟩ | 4-(CH$_3$O)—C$_6$H$_4$— | cis |
| −N⟨piperidine⟩ | 4-(CH$_3$O)—C$_6$H$_4$— | trans |
| −N⟨thiomorpholine⟩S | 4-(CH$_3$O)—C$_6$H$_4$— | cis |
| −N⟨thiomorpholine⟩S | 4-(CH$_3$O)—C$_6$H$_4$— | trans |
| −N⟨dioxaspiro⟩ | 4-(CH$_3$O)—C$_6$H$_4$— | cis |
| −N⟨dioxaspiro⟩ | 4-(CH$_3$O)—C$_6$H$_4$— | trans |
| −N⟨piperazine⟩NCH$_3$ | C$_6$H$_5$— | cis |
| −N⟨piperazine⟩NCH$_3$ | C$_6$H$_5$— | trans |
| −N⟨piperazine⟩NH | 4-(CH$_3$O)—C$_6$H$_4$— | trans |

-continued
| | | |
|---|---|---|
| 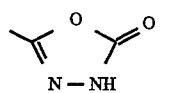 | 4-(CH₃O)—C₆H₄— | trans |
| 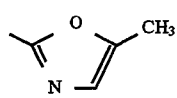 | 4-(CH₃O)—C₆H₄— | trans |
2. A method of lowering serum cholesterol levels in a mammal in need of such treatment comprising administering an effective amount of a compound of claim 1.
3. A pharmaceutical composition comprising a cholesterol-lowering effective amount of a compound of claim 1 in a pharmaceutically acceptable carrier.
* * * * *